United States Patent [19]

Plueddemann

[11] 4,071,546
[45] Jan. 31, 1978

[54] SILICON-CONTAINING CHELATING COMPOSITION AND METHOD THEREFOR

[75] Inventor: Edwin P. Plueddemann, Midland, Mich.

[73] Assignee: Dow Corning Corporation, Midland, Mich.

[21] Appl. No.: 719,015

[22] Filed: Aug. 30, 1976

[51] Int. Cl.$^2$ .............................................. C07F 7/10
[52] U.S. Cl. ............................................. 260/448.2 N
[58] Field of Search ................................ 260/448.2 N

[56] References Cited

U.S. PATENT DOCUMENTS

| 3,725,302 | 4/1973 | Shimely et al. | 260/448.2 N X |
| 3,892,678 | 7/1975 | Halasz et al. | 260/448.2 N X |

Primary Examiner—Paul F. Shaver
Attorney, Agent, or Firm—George A. Grindahl

[57] ABSTRACT

New organosiloxane chelating compositions comprising a siliceous support and an organosiloxane chelating agent bonded to its surface are disclosed. A new method for preparing the composition comprises contacting the siliceous support with a solution of an organosiloxane comprising units of the formula

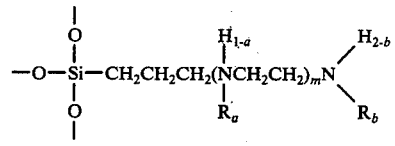

and optionally, units of the formula

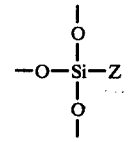

R is —CH$_2$COOH or —CH$_2$COO$^-$M+; M+ is an alkali metal ion, $m = 0$ or 1, $a = 0$ or 1, $b = 1$ or 2, $(m \cdot a) + b$ is at least 2 and Z is a monovalent hydrocarbon radical having 1 to 6 inclusive carbon atoms.

17 Claims, No Drawings

SILICON-CONTAINING CHELATING COMPOSITION AND METHOD THEREFOR

BACKGROUND OF THE INVENTION

This invention relates to silicon-containing chelating agents. In one aspect, his invention relates to a siliceous surface bearing an organosiloxane chelating agent which is suitable for chelating polyvalent metal ions.

It is well known to treat a siliceous surface, with a suitable hydrolyzable organosilane thereby bonding organic radicals to the siliceous surface. For example, there are currently available certain controlled pore glass supports bearing various organic radicals which are bonded to the glass through Si—O—Si—C bonds to produce protein-active supports. Recently, Leyden, et al., Anal. Chem., 47 (a), pp. 1612 to 1617, August 1975, silylated silica gel with various aminoalkyltrimethoxysilanes to immobilize the various aminoalkyl radicals onto the silica gel. The immobilized aminoalkyl radicals were subsequently derivatized to the corresponding dithiocarbamate and thereafter employed to preconcentrate trace amounts of certain metal ions from dilute solution for subsequent X-ray analysis.

The method of Leyden, et al. is suitable for preparing small amounts of immobilized chelating agents but is less desirable for producing large amounts of said chelating agents. For example, it is undesirable to process a large amount of the support material during the silylating step and again during the subsequent derivatizing step. A more efficient process is desired. There is also a need for inexpensive, immobilized chelating agents for chelating polyvalent metal ions such as calcium ions and magnesium ions.

It is also well known to produce chelating agents which are suitable for chelating polyvalent metal ions such as $Ca^{+2}$, by derivatizing certain polyamines such as ethylenediamine with carboxymethyl groups. The resulting chelating agents such as ethylenediaminetetraacetic acid, diethylenetriaminepentaacetic acid and nitrilotriacetic acid and their salts are readily available.

Prior to this invention, it had not been known or suggested to prepare silicon-containing materials bearing carboxymethyl derivatives of silicon-bonded aminoalkyl radicals, or to bond said materials to a siliceous support.

Herein, aminoalkyl radical means an organic radical bearing at least one nitrogen atom which is bonded to at least one aliphatic carbon atom. Silicon-bonded aminoalkyl radicals are bonded to the silicon through a silicon-carbon bond. By polyvalent metal ions it is meant those metal ions having a positive charge greater than +1 such as $Fe^{+3}$, $Th^{+4}$, $Hg^{+2}$, $Cu^{+2}$, $Ni^{+2}$, $Pb^{+2}$, $Zn^{+2}$, $Al^{+3}$, $Fe^{+2}$, $Mn^{+2}$, $Ca^{+2}$, $Mg^{+2}$, $Ba^{+2}$, and the rare earth ions.

SUMMARY OF THE INVENTION

It is an object of this invention to provide new silicon-containing chelating agents which are suitable for chelating polyvalent metal ions.

It is another object of this invention to provide an improved method for preparing immobilized chelating agents.

It is a further object of this invention to provide new compositions which are useful for preparing immobilized chelating agents.

These and other objects will be obvious after considering the following disclosure and appended claims.

This invention relates to new silicon-containing solutions comprising certain carboxymethyl derivatives of silicon-bonded aminoalkyl groups. The solutions may be prepared in a suitable solvent and the resulting solution may then be used to apply the silicon-containing chelating agent to the siliceous support. The resulting treated siliceous support may be used to chelate polyvalent metal ions such as in a water softening process. The solutions have other uses such as being admixed with a silicone resin composition to chelate deleterious polyvalent metal ions which may be present in the resin. This invention further relates to the siliceous support having bonded to the surface thereof, certain carboxymethyl derivatives of silicon-bonded aminoalkyl groups.

DESCRIPTION OF THE INVENTION

In one aspect this invention relates to a composition comprising a siliceous support having bonded to the surface thereof an organosiloxane consisting essentially of at least 50 mol percent of (A) siloxane units having the formula

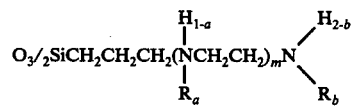

wherein R is $—CH_2COOH$ or $—CH_2COO^-M^+$, $M^+$ is an alkali metal anion, $m$ is 0 or 1, $a$ is 0 or 1, and $b$ is 1 or 2, the total of $(m·a) + b$ having a value of at least 2; and up to 50 mol percent of (B) siloxane units having the formula

wherein Z is a monovalent hydrocarbon radical having from 1 to 6 inclusive carbon atoms, the total of (A) and (B) being 100 mol percent.

The siliceous support may be any suitable solid that comprises silanol sites at its surface such as glass, sand, quartz, diatomaceous earth and silica gel. It should be understood that by solid it is meant both void-free solids such as a glass plate and glass fibers and void-containing solids such as controlled pore glass, hollow glass fibers, and diatomaceous earths. A preferred form of the siliceous support is a finely-divided siliceous support such as ground quartz, ground diatomaceous earth, glass fibers, sand particle, and silica having a low surface area such as less than approximately 10 square meters of area per gram of silica. Finely-divided siliceous solids are commonly used as filtering media and are eminently adaptable for preparing an inexpensive composition of this invention which is useful for treating large volumes of solution comprising polyvalent metal ions such as $Ca^{+2}$ or $Mg^{+2}$, such as hard water.

The organosiloxane which is bonded to the surface of the siliceous support consists essentially of siloxane units having the formula

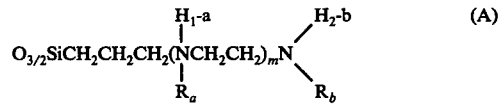

and optionally, siloxane units having the formula

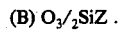

It is well known to copolymerize siloxane units of the type (B) with known siloxane units of the art for various reasons such as to improve bonding of the resulting copolysiloxane to a surface or to provide a less expensive copolysiloxane or to provide improved performance of the other siloxane units in the copolysiloxane. Organosiloxanes having trace amounts of other siloxane units such as $SiO_{4/2}$, $Z_2SiO_{2/2}$ and $X_3SiO_{1/2}$ are deemed to be within the scope and spirit of this invention.

Z may be any monovalent hydrocarbon radical having from 1 to 6 carbon atoms such as methyl, ethyl, isopropyl, vinyl, cyclohexyl and phenyl. Z is preferably methyl.

The amount of (B) siloxane units in the organosiloxane is from none to 50 mol percent inclusive, based on the total number of siloxane units in the organosiloxane. Organosiloxanes wherein all of the siloxane units are of the (A) type are preferred because they possess good chelating ability and are simpler to prepare than organosiloxanes bearing additional (B) siloxane units.

The amount of (A) siloxane units in the organosiloxane is at least 50 mol percent, and preferably 100 mol percent.

The (A) siloxane units bear derivatized, silicon-bonded -aminopropyl radicals (m=0) or N-β-aminoethyl-aminopropyl radicals (m=1) which contain carboxymethyl radicals, R, bonded to nitrogen atoms. By carboxymethyl radical it is meant $-CH_2COOH$, or its ionized form $-CH_2COO^-H^+$, or its alkali metal salt $-CH_2COO^-M^+$. M is preferably the sodium anion; however, it may optionally be the lithium, potassium, rubidium, or cesium anion. It is to be understood that the hydrogen ion of the ionized carboxymethyl radical, $-CH_2COO^-H^+$, may be associated with any suitable site within the organosiloxane such as the $-CH_2COO^-$ radical or any amino nitrogen atom.

It has been found that suitable chelating ability is not obtained if R is other than carboxymethyl, e.g. carboxyethyl. It has also been found that efficient chelating ability is not obtained if the (A) siloxane units of the organopolysiloxane have fewer than two, e.g. one or zero carboxymethyl radicals per aminoalkyl radical, i.e. per (A) siloxane unit. Of course, if some of the aminoalkyl radicals bear at least two carboxymethyl radicals and the remainder of the aminoalkyl radicals bear less than two carboxymethyl radicals, the organosiloxane will still possess some chelating ability, but such an organosiloxane would be less efficient in chelating ability than an organosiloxane wherein every (A) siloxane unit possesses at least two carboxymethyl radicals and would be wasteful of the silicon-bonded aminoalkyl radicals.

The organosiloxane of this invention may have (A) siloxane units which bear only carboxymethyl derivatives of γ-aminopropyl radicals or only carboxymethyl derivatives of N-β-aminoethyl-γ-aminopropyl radicals. The (A) siloxane units may also be any mixture of said siloxane units bearing the carboxymethyl aminoalkyl radicals.

For example, the organosiloxane of this invention may comprise (A) siloxane units which are only $O_{3/2}SiCH_2CH_2CH_2NR_2$ or only $O_{3/2}SiCH_2CH_2CH_2NHCH_2CH_2NR_2$ or only $O_{3/2}SiCH_2CH_2CH_2N(R)CH_2CH_2NHR$ or only $O_{3/2}SiCH_2CH_2CH_2N(R)-CH_2CH_2NR_2$ or any of their mixtures wherein R is as defined elsewhere herein. It should also be understood that the organosiloxane of this invention may comprise small amounts of siloxane units bearing less than two R radicals such as $O_{3/2}SiCH_2CH_2CH_2NHR$, $O_{3/2}SiCH_2CH_2CH_2NHCH_2CH_2NHR$, $O_{3/2}SiCH_2CH_2CH_2N(R)CH_2CH_2NH_2$, $O_{3/2}SiCH_2CH_2CH_2NH_2$ and $O_{3/2}SiCH_2CH_2CH_2NHCH_2CH_2NH_2$; however, to the extent that these partially derivatized aminoalkyl radicals are present, the chelating capacity of the resulting organosiloxane will be correspondingly reduced.

A preferred organosiloxane of this invention consists essentially of 100 mol percent of siloxane units having the formula $O_{3/2}SiCH_2CH_2CH_2N(CH_2COO^-NA^+)_2$.

Another preferred organosiloxane of this invention consists essentially of 100 mol percent of siloxane units having the formula

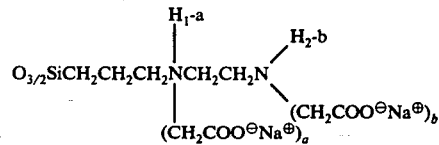

wherein the average value of $a + b$ is from 2 to 3 inclusive.

The organosiloxane is bonded to the siliceous support with sufficient strength so that it cannot be rinsed from said support with aqueous slurrying. While not wanting to be limited by theory, I believe the organosiloxane is bonded to the siliceous support at least in part with at least one $-Si-O-Si-$ bond wherein one of the silicon atoms of the $-Si-O-Si-$ bond is contributed by the surface of the siliceous support and the other silicon atom is contributed by the organosiloxane. Of course, an organopolysiloxane molecule having several siloxane units may have several bonds to the siliceous surface. It is to be understood that the organosiloxane may also be bonded to the surface of the siliceous support by other means such as hydrogen bonding and/or, due to the polymer structure of the organosiloxane, by simple encapsulation of a siliceous particle by the organosiloxane, as long as it cannot be removed by water slurrying.

While it is believed that the organosiloxane has a silsesquioxane structure, i.e. essentially all silicon atoms of the organosiloxane are bonded to other silicon atoms, including organosiloxane silicon atoms and siliceous support silicon atoms, by way of divalent oxygen atoms, an organosiloxane wherein the silicon atoms also bear small amounts of silicon-bonded hydroxyl radicals and/or silicon-bonded lower alkoxy radicals is within the scope and spirit of this invention.

The composition of this invention may be prepared in any suitable manner. For example, a suitable siliceous support may be treated with an organosilane bearing aminoalkyl radicals, such as $(CH_3O)_3SiCH_2CH_2CH_2NH_2$, thereby bonding the aminoalkyl radicals to the siliceous support and also condensing organosilane molecules by way of siloxane bonds. Thereafter, the aminoalkyl radicals which are bonded to the siliceous support may be converted to the carboxymethyl derivative by reaction with a suitable reagent such as chloroacetic acid in the presence of an HCl acceptor.

A preferred method for preparing the composition of this invention comprises contacting a siliceous support with a solution of an organosilicon solute bearing silicon-bonded aminoalkyl radicals which have been derivatized with carboxymethyl radicals.

To this end, this invention further relates to a solution comprising a solvent and an organosilicon solute dissolved in said solvent, said solvent being selected from the group consisting of water and organic solvents, said organosilicon solute consisting essentially of at least 50 mol percent of (I) organosilicon compounds having the formula

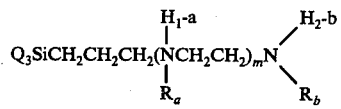

or hydrolyzates thereof and up to 50 mol percent of (II) organosilicon compounds having the formula $Q_3SiZ$ or hydrolyzates and cohydrolyzates thereof, the total of (I) and (II) being 100 mol percent, Q being a lower alkoxy radical and R, Z, a and b are as defined hereinabove, the total of $(m \cdot a) + b$ having a value of at least 2.

The solutions of this invention are uniquely adapted for use in preparing the aforementioned compositions of this invention. The solutions of this invention have additional utility, such as a minor component in a silicone resin whereby the organosiloxane chelates trace amounts of deleterious polyvalent metal ions which may be present in the resin and additionally the organosiloxane chelating agent is incorporated into the silicone resin matrix by way of reaction of the lower alkoxy radicals.

Q is a lower alkoxy radical of from 1 to 6 inclusive carbon atoms, and preferably from 1 to 4 carbon atoms, such as methoxy, ethoxy, isopropoxy, butoxy, vinyloxy, allyloxy, and cyclohexoxy. Q is most advantageously methoxy.

Organic solvents which are suitable for preparing the solutions of this invention include, aromatic hydrocarbons such as benzene, toluene, and xylene; alcohols such as monohydric alcohols such as methanol, ethanol, and isopropanol and polyhydric alcohols such as ethylene glycol, propylene glycol and glycerine; ether alcohols such as the monomethyl ether of ethylene glycol or the monoethyl ether of diethylene glycol; and ethers such as diethyl ether, tetrahydrofuran, dioxane and polyethers such as ethylene glycol dimethyl ether and diethylene glycol dimethyl ether. Water-miscible organic solvents are preferred.

To prepare the compositions of this invention using the solutions of this invention, the solutions are appropriately adapted. Thus, to prepare a preferred composition hereinbefore disclosed, for example a siliceous support having bonded to the surface thereof an organosiloxane consisting essentially of 100 mol percent (A) siloxane units, the appropriate siliceous support is contacted with a solution of this invention wherein the organosilicon solute is adapted to consist essentially of 100 mole percent of (I) organosilicon compounds or hydrolyzates thereof.

A highly preferred solution of this invention comprises water as the solvent, in major amounts. In addition, a preferred aqueous solution of this invention is obtained when R is $-CH_2COO^-Na^+$. Aqueous solutions of this invention are preferred in processes wherein the presence of an organic solvent is undesired for various reasons such as for safety, pollution, and economic considerations.

Aqueous solutions of this invention comprise hydrolyzates of

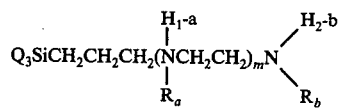

and, when present, $Q_3SiZ$ .

By hydrolyzates thereof, it is meant organosilanes and organosiloxane that result when one or more Q radicals are removed by the action of water from the silicon atom of (I) and/or (II) to form the corresponding alcohol QH, e.g. $CH_3OH$, and is replaced by a hydroxyl radical to produce the corresponding silanol $\equiv SiOH$. This silanol may or may not react with a $\equiv SiQ$ or another $\equiv SiOH$ to produce an organosiloxane. Dilute aqueous solutions of hydrolyzable organosilicon compounds such as (I) and (II) are, consequently, complicated mixtures of organosilanes and organosiloxanes bearing varying amounts of silicon-bonded Q radicals and silicon-bonded OH radicals. By cohydrolyzates it is meant that there may be present in the aqueous solution siloxanes wherein there is at least one siloxane unit bearing a Z radical and at least one siloxane unit bearing a derivatized aminoalkyl radical. Alkaline aqueous solutions may also comprise silanolate species such as $\equiv Si-O^-Na^+$.

The solutions of this invention may be prepared in any suitable manner. For example an aminoalkylsilane such as one molar part of $(CH_3O)_3SiCH_2CH_2CH_2NH_2$ may be mixed with two molar parts of $ClCH_2COOH$ in the presence of a sufficient amount of an HCl acceptor such as triethylamine to absorb the liberated HCl and a solvent such as methanol to give rise to an organic solvent solution comprising $(CH_3O)_3SiCH_2CH_2CH_2N(CH_2COOH)_2$. Said solution may be converted to an aqueous solution by the addition of water and then used to prepare the compositions of this invention. Alternately, the organic solvent solution may be used in the anhydrous form to prepare said compositions.

The highly preferred aqueous solutions of this invention may be prepared by any suitable method. For example, one molar part of $(CH_3O)_3SiCH_2CH_2CH_2NHCH_2CH_2NH_2$ may be admixed with 3 molar parts of NaOH in water. Sodium chloroacetate may then be admixed with the aqueous alkaline solution to produce a hydrolyzate of $(CH_3O)_3SiCH_2CH_2CH_2N(CH_2COO^-Na^+)CH_2CH_2N(CH_2COO^-Na^+)_2$. This solution comprising water and said hydrolyzate may be used as prepared or it may be further modified. For example, the solution may be diluted with solvent such as water and/or a water-miscible organic solvent. Also, the solution may be adjusted in pH value as long as the organosiloxane hydrolyzate does not gel before it is contacted with a siliceous support.

The solutions of this invention are stable for months. The aqueous solutions of this invention are surprisingly stable and are especially useful for preparing the compositions of this invention.

This invention further relates to a method for preparing a treated siliceous support comprising (i) contacting a siliceous support with a solution of this invention to produce a treated siliceous support having bonded to the surface thereof a chelating agent suitable for chelating polyvalent metal ions and (ii) separating the treated siliceous support from essentially all of the solution which is not bonded to the surface of the siliceous support.

The siliceous support may be contacted with the solution of this invention in any suitable manner such as by slurrying, tumbling, soaking, rinsing, and spraying and in such a way as to insure intimate contact between said support and said solution.

The contacting may be conducted at any suitable temperature above the freezing point of the solution but not exceeding the boiling point of the solution. Preferably, the contacting is done at approximately ambient temperature. After the contacting step has been conducted for a suitable length of time, said time being inversely related to the temperature at which the contacting is conducted to treat the siliceous support, the resulting treated siliceous support is separated from the unbonded portion of the solution.

The separating may be conducted by any suitable method such as filtering, draining, decanting, centrifuging and rinsing and in such a manner as to remove essentially all of the solution which is not bonded to the siliceous support. Thereafter, the treated support may be heated mildly, e.g. from greater than room temperature to approximately 150° C. to dry the treated siliceous support and to promote further reaction of the bonded portion of the solution with itself and with the siliceous support.

The product of the method of this invention is a treated siliceous support such as a finely-divided siliceous support having bonded to the surface thereof a chelating agent suitable for chelating polyvalent metal ions. The chelating capacity of the treated siliceous supports of this invention may be measured in the well-known manner comprising titrating the treated siliceous support with standard $Ca^{+2}$ solution in the presence of ammonium oxalate indicator. Spent chelating capacity may be regenerated in the common manner, i.e. rinsing the spent composition with alkali metal ion solutions or hydrogen ion solutions.

The following Examples are for illustration and not for limitation of the invention. The invention is properly delineated by the appended claims.

EXAMPLE 1

This example illustrates the preparation of the solutions of this invention.
$(CH_3O)_3SiCH_2CH_2CH_2NHCH_2CH_2NH_2$, 22 g. (0.1 mol) was added to 24 g. (0.6 mol) of NaOH dissolved in 76 g. of $H_2O$. The solution, which became warm during the addition, was cooled and 28.5 g. (0.3 mols) of $ClCH_2COOH$ was added to the cooled solution. Again the solution became warm. There was obtained 150 g. of a clear solution (sample 1) comprising water and the hydrolyzate of $(CH_3O)_3SiCH_2CH_2CH_2N(CH_2COO^-$ $Na^+)CH_2CH_2N(CH_2COO^-Na_+)_2$. The clear solution also contained dissolved NaCl and methanol. Using apropriate quantities of the same components there was prepared similar clear solutions wherein the hydrolyzate contained 2.5 (sample 2), 2.0 (sample 3), and 1.0 (sample 4) $-CH_2COO^-Na^+$ radicals for every N-β-aminoalkyl-γ-aminopropyl radical in the hydrolyzate. The preparation was repeated using 0.1 gram mol of $(CH_3CH_2O)_3SiCH_2CH_2CH_2NH_2$, 16 g. of NaOH in 43 g. of water and 19 g. of chloroacetic acid. A clear solution (sample 5) comprising the hydrolysis product of $(CH_3CH_2O)_3SiCH_2CH_2CH_2N(CH_2COO^-Na^+)_2$ was obtained.

The chelating capacity of a chelating agent was determined by dissolving 5 grams of each of the clear solutions described above (and containing a known amount of chelating agent) in 20 ml. distilled water. Saturated ammonium oxalate solution, 1.5 ml. was added and the solution was titrated with a standard $CaCl_2$ solution containing $Ca^{+2}$ equivalent to 50 mg. of $CaCO_3$ solution of standard solution. The amount of standard $CaCl_2$ solution that was needed to provide permanent turbidity of the sample at a pH greater than 11.0 was noted. The chelating capacity of the chelating agent was calculated by using the formula $$\text{Chelating capacity} = \frac{(\text{ml. CaCl}_2 \text{ sol.}) \times 50}{(\text{grams of chelating agent})} = \frac{\text{mg. CaCO}_3}{\text{grams of chelating agent}}$$

The chelating capacity may also be expressed as mols of $CaCO_3$ per mol of aminoalkyl radicals. For comparison, the chelating capacity of the hydrolyzate of $(CH_3O)_3SiCH_2CH_2CH_2NHCH_2CH_2NH_2$ (sample 6), the trisodium salt of nitrilotriacetic acid (sample 7) and the tetrasodium salt of ethylene diaminetetraacetic acid (sample 8) were measured. Sample solutions of these well-known chelating agents (samples 7 and 8) were prepared by dissolving 1.0 g. of the chelating agent in 25 ml. of water.

Titration of the above-described solutions (samples 1 to 5) was done one hour after said solutions were prepared and also after said solutions were heated at 50° C. for 4 hours. Results are summarized in Table I. This shows that solutions of this invention wherein the organosilicon solute bears more than 2 carboxymethyl radicals per aminoalkyl have excellent chelating capacity but may require more than one hour at ambient temperature to develop this capacity.

TABLE I

| Sample | Ratio —CH$_2$COONa radicals aminoalkyl group | Chelating Capacity | | | |
|---|---|---|---|---|---|
| | | mg. CaCO$_3$/g. chelating agent | | mols CaCO$_3$/mol aminoalkyl radicals | |
| | | 1 hr. after prep. | 4 hr./50° C. | 1 hr. after prep. | 4 hr./50° C. |
| 1 | 3.0/1 | 126 | 244 | 0.50 | 0.96 |
| 2 | 2.5/1 | 224 | 254 | 0.79 | 0.90 |
| 3 | 2.0/1 | 153 | 173 | 0.48 | 0.54 |
| 4* | 1.0/1 | 26 | 26 | 0.06 | 0.06 |
| 5 | 2.0/1 | 325 | 325 | 0.65 | 0.65 |
| 6* | zero | 7 | — | Trace | — |
| 7* | 3.0/1 | 365 | — | 0.94 | — |
| 8* | 4.0/1 | 250 | — | 0.95 | — |

*For comparison

EXAMPLE 2

This example illustrates the preparation of a treated siliceous support.

Samples 3 and 7 were diluted with water to provide a solution having 1 weighted percent chelating agent. E-Glass fibers were milled through ¼" mesh and 10 gram samples of the glass fibers were slurried with the diluted solutions 3 and 7 for 1 hour. The treated fibers were filtered and were dried at room temperature for 4 days. The dried fibers were then slurried with 300 ml. of distilled water in a Waring Blendor and filtered to rinse off unbonded chelating agent.

Fifty milliliter portions of hard water (80 p.p.m. CaCO$_3$) were percolated through the moist filter residue of treated glass fibers. The percolated water was then titrated with standard soap solution to determine its hardness. Table II shows that the glass fibers that were treated with the known chelating agent (Sample 7), trisodium nitrilotricetate, did not remove any hardness from the hard water, thus showing that the chelating agent was not bonded to the glass fibers and was rinsed off with the 300 ml. portion of rinse water. Table II also shows that the treated glass fibers of this invention reduced the hardness of two 50 ml. portions of the hard water before it became ineffective. The spent treated glass fibers of this invention were regenerated to their original chelating ability by slurrying the spent fibers with saturated NaCl solution for 15 minutes, filtering and rinsing the regenerated glass fibers until the filtrate was free of NaCl as indicated by only faint turbidity when mixed with dilute AgNO$_3$ solution. Table II shows the chelating ability of the regenerated glass fibers. This example shows that the chelating agent of this invention is bonded to the siliceous support and is an effective chelating composition for calcium ion.

TABLE II

| Number of 50 ml. percolations with hard water | Hardness of water after being percolated through treated glass fibers | |
|---|---|---|
| | Sample 3 | Sample 7 |
| 1 | 50 | 130 |
| 2 | 60 | 80 |
| 3 | 80 | — |
| Regeneration | | |
| 4 | 50 | — |
| 5 | 65 | — |
| 6 | 80 | — |

That which is claimed is:

1. A composition comprising a siliceous support having bonded to the surface thereof an organosiloxane consisting essentially of at least 50 mol percent of
   A. siloxane units having the formula

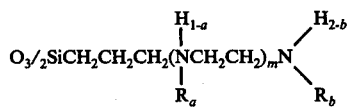

wherein R is —CH$_2$COOH or —CH$_2$COO$^-$M$^+$, M$^+$ is an alkali metal anion, $m$ is 0 or 1, $a$ is 0 or 1 and $b$ is 1 or 2, the total of $(m \cdot a) + b$ having a value of at least 2; and up to 50 mol percent of
   B. siloxane units having the formula $O_{3/2}SiZ$ wherein Z is a monovalent hydrocarbon radical having from 1 to 6 inclusive carbon atoms, the total of (A) and (B) being 100 mol percent.

2. The composition of claim 1 wherein the siliceous support is a finely divided siliceous support.

3. The composition of claim 2 wherein the organosiloxane consists essentially of 100 mol percent of (A) siloxane units.

4. The composition of claim 3 wherein R is —CH$_2$COO$^-$M$^+$ and M+ is Na$^+$.

5. The composition of claim 4 wherein $m$ is 1 and the total of $a + b$ has an average value of from 2 to 3 inclusive.

6. The composition of claim 4 wherein $m$ is 0 and $b$ is 2.

7. A solution comprising a solvent and an organosilicon solute dissolved in said solvent, said solvent being selected from the group consisting of water and common organic solvents, said organosilicon solute consisting essentially of at least 50 mol percent of
   I. organosilicon compounds having the formula

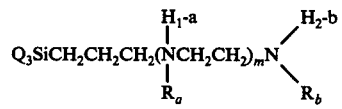

or hydrolyzates thereof, wherein Q is a lower alkoxy radical, R is —CH$_2$COOH or —CH$_2$COO$^-$M$^+$, M$^+$ is an alkali metal ion, $m$ is 0 or 1, $a$ is 0 or 1, $b$ is 1 or 2, the total of $(m \cdot a) + b$ having a value of at least 2, and up to 50 mol percent of
   II. organosilicon compounds having the formula $Q_3SiZ$ or hydrolyzates and cohydrolyzates thereof, wherein Q is a lower alkoxy radical and Z is a monovalent hydrocarbon radical having from 1 to 6 inclusive carbon atoms, the total of (I) and (II) being 100 mol percent.

8. The solution of claim 7 wherein the organosilicon solute consists essentially of 100 mol percent of organosilicon compounds (I) or hydrolyzates thereof.

9. The solution of claim 8 wherein the solvent comprises water.

10. The solution of claim 9 wherein R is —CH$_2$COO$^-$M$^+$ and M$^+$ is Na$^+$.

11. The solution of claim 10 wherein Q is —OCH$_3$, $m$ is 1 and the total of $a + b$ has an average value of from 2 to 3 inclusive.

12. The solution of claim 10 wherein Q is —OCH$_3$, $m$ is 0 and $b$ is 2.

13. A method for preparing a treated siliceous support comprising
   i. contacting a siliceous support with the solution of claim 7 to produce a treated siliceous support having bonded to the surface thereof a chelating agent suitable for chelating polyvalent metal ions,
   ii. separating the treated siliceous support from essentially all of the composition of claim 7 which is not bonded to the surface of the siliceous support.

14. The method in accordance with claim 13 wherein the treated siliceous support is heated to a temperature of from greater than room temperature to approximately 150° C.

15. The method in accordance with claim 13 wherein the siliceous support is a finely-divided siliceous support.

16. The method in accordance with claim 15 wherein the solution comprises water and the organosilicon solute consists essentially of 100 mol percent of the hydrolyzate of organosilicon compounds having the formula (CH$_3$O)$_3$SiCH$_2$CH$_2$CH$_2$NR$_2$ wherein R is —CH$_2$COOH or —CH$_2$COO$^-$M$^+$ and M$^+$ is an alkali metal ion.

17. The method in accordance with claim 15 wherein the solution comprises water and the organosilicon solute consists essentially of 100 mol percent of the hydrolyzate of organosilicon compounds having the formula

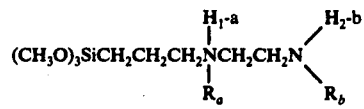

wherein R is —CH$_2$COOH or —CH$_2$COO$^-$M$^+$, M$^+$ is an alkali metal ion, $a$ is 0 or 1, $b$ is 1 or 2, the total of $a + b$ having an average value of from 2 to 3 inclusive.

* * * * *

UNITED STATES PATENT AND TRADEMARK OFFICE
CERTIFICATE OF CORRECTION

PATENT NO. : 4,071,546
DATED : January 31, 1978
INVENTOR(S) : Edwin P. Plueddemann It is certified that error appears in the above-identified patent and that said Letters Patent are hereby corrected as shown below:

Column 1, line 7, the word "his" should read --this--.

Column 3, line 8, the formula "$X_3SiO_{1/2}$" should read --$Z_3SiO_{1/2}$--.

Column 3, line 66, the formula "$SiCH_2CH_2CH_2N(R)-CH_2CH_2NR_2$" should read --$SiCH_2CH_2CH_2N(R)CH_2CH_2NR_2$--.

Column 4, line 6, the formula "$SICH_2CH_2CH_2NH_2$" should read --$SiCH_2CH_2CH_2NH_2$--.

Column 5, line 6, the word "sadi" should read --said--.

Column 8, lines 2-3, the formula should read
--$(CH_3O)_3SiCH_2CH_2CH_2N(CH_2COO^-Na^+)CH_2CH_2N(CH_2COO^-Na^+)_2$--.

Column 8, line 23, after the formula "$CaCO_3$" "solution" should read -- per ml. --.

Column 9, line 10, the word "Fity" should read --Fifty--.

Column 10, Claim 4, second line, "M+" should read --$M^+$--.

Signed and Sealed this

Eighteenth Day of November 1980

[SEAL]

Attest:

SIDNEY A. DIAMOND

Attesting Officer   Commissioner of Patents and Trademarks